United States Patent
Pogosyan et al.

(10) Patent No.: US 10,387,265 B1
(45) Date of Patent: Aug. 20, 2019

(54) PREVENTIVE HASH LOADING

(71) Applicant: Acronis International GmbH, Shaffhausen (CH)

(72) Inventors: Vitaly Pogosyan, Mytishchi (RU); Andrey Panin, Moscow (RU); Stanislav Protasov, Moscow (RU); Serguei M. Beloussov, Costa del Sol (SG)

(73) Assignee: ACRONIS INTERNATIONAL GMBH (CH)

( * ) Notice: Subject to any disclaimer, the term of this patent is extended or adjusted under 35 U.S.C. 154(b) by 315 days.

(21) Appl. No.: 14/971,360

(22) Filed: Dec. 16, 2015

Related U.S. Application Data

(60) Provisional application No. 62/098,436, filed on Dec. 31, 2014.

(51) Int. Cl.
*G06F 17/00* (2019.01)
*G06F 11/14* (2006.01)
*G11C 7/10* (2006.01)

(52) U.S. Cl.
CPC ...... *G06F 11/1451* (2013.01); *G06F 11/1435* (2013.01); *G06F 11/1464* (2013.01); *G11C 7/1072* (2013.01); *G06F 2201/80* (2013.01); *G06F 2201/84* (2013.01)

(58) Field of Classification Search
CPC ............. G06F 11/1451; G06F 11/1469; G06F 2201/84; G06F 11/1417; G06F 11/1466
USPC ....................................... 707/704
See application file for complete search history.

(56) References Cited

U.S. PATENT DOCUMENTS

| | | | |
|---|---|---|---|
| 7,047,380 B2 | 5/2006 | Tormasov et al. |
| 7,246,211 B1 | 7/2007 | Beloussov et al. |
| 7,275,139 B1 | 9/2007 | Tormasov et al. |
| 7,281,104 B1 | 10/2007 | Tsypliaev et al. |
| 7,318,135 B1 | 1/2008 | Tormasov et al. |
| 7,353,355 B1 | 4/2008 | Tormasov et al. |
| 7,366,859 B2 | 4/2008 | Per et al. |
| 7,475,282 B2 | 1/2009 | Tormasov et al. |
| 7,603,533 B1 | 10/2009 | Tsypliaev et al. |
| 7,636,824 B1 | 12/2009 | Tormasov |
| 7,650,473 B1 | 1/2010 | Tormasov et al. |
| 7,721,138 B1 | 5/2010 | Lyadvinsky et al. |
| 7,779,221 B1 | 8/2010 | Tormasov et al. |
| 7,831,789 B1 | 11/2010 | Tsypliaev et al. |
| 7,886,120 B1 | 2/2011 | Tormasov |

(Continued)

*Primary Examiner* — Truong V Vo
(74) *Attorney, Agent, or Firm* — K&L GATES LLP

(57) ABSTRACT

A method, computer program product, computing system, and system for preventive hash loading are described. The method may include receiving an indication at a storage server that a machine will be backed up. The method may further include loading fingerprints of blocks related to a previous backup of the machine to RAM of the storage server. The method may also include searching the storage server for fingerprints in the RAM that match fingerprints of incoming blocks from the machine being backed up. The method may additionally include, in response to determining that the fingerprints of the incoming blocks do not match fingerprints in the RAM, searching for the fingerprints in a database. Moreover, the method may include transferring only blocks from the machine being backed up that are not in the RAM or the database of the storage server to the storage server.

16 Claims, 3 Drawing Sheets

(56) References Cited

U.S. PATENT DOCUMENTS

| | | | |
|---|---|---|---|
| 7,895,403 B1 | 2/2011 | Tormasov et al. | |
| 7,934,064 B1 | 4/2011 | Per et al. | |
| 7,937,612 B1 | 5/2011 | Tormasov et al. | |
| 7,949,635 B1 | 5/2011 | Korshunov et al. | |
| 7,953,948 B1 | 5/2011 | Dyatlov et al. | |
| 7,979,690 B1 | 7/2011 | Dyatlov et al. | |
| 8,005,797 B1 | 8/2011 | Chepel et al. | |
| 8,051,044 B1 | 11/2011 | Dyatlov et al. | |
| 8,069,320 B1 | 11/2011 | Per et al. | |
| 8,073,815 B1 | 12/2011 | Korshunov et al. | |
| 8,074,035 B1 | 12/2011 | Per et al. | |
| 8,145,607 B1 | 3/2012 | Korshunov et al. | |
| 8,180,984 B1 | 5/2012 | Per et al. | |
| 8,225,133 B1 | 7/2012 | Tormasov et al. | |
| 8,261,035 B1 | 9/2012 | Tormasov et al. | |
| 8,296,264 B1 | 10/2012 | Dyatlov et al. | |
| 8,312,259 B1 | 11/2012 | Dyatlov et al. | |
| 8,347,137 B1 | 1/2013 | Chepel et al. | |
| 8,484,427 B1 | 7/2013 | Lyadvinsky et al. | |
| 8,645,748 B1 | 2/2014 | Chepel et al. | |
| 8,732,121 B1 | 5/2014 | Zorin et al. | |
| 8,856,927 B1 | 10/2014 | Beloussov et al. | |
| 8,996,830 B1 | 3/2015 | Lyadvinsky et al. | |
| 2006/0225065 A1 | 10/2006 | Chandhok et al. | |
| 2010/0011178 A1 | 1/2010 | Feathergill | |
| 2014/0279956 A1* | 9/2014 | Trimble | G06F 3/0641 707/692 |
| 2015/0019507 A1* | 1/2015 | Aronovich | G06F 17/30156 707/692 |

\* cited by examiner

PREVENTIVE HASH LOADING

CROSS-REFERENCE TO RELATED APPLICATIONS

This application claims priority to and the benefit of U.S. Provisional Patent Application No. 62/098,436 filed on Dec. 31, 2014, the disclosure of which IS herein incorporated by reference in its entirety.

TECHNICAL FIELD

The technical field may generally relate to backup of physical or virtual machines and more particularly to reducing an amount of data transmitted during backup of physical or virtual machines.

BACKGROUND

Physical or virtual machines may run business critical or other applications. An entire physical or virtual machine or individual files or folders of the physical or virtual machine may require backup to ensure that the physical or virtual machine may be recovered in the event of a failure. Such backup of a physical or virtual machine may be difficult to create because backup processes may consume too many resources, causing low performance or high network load. For example, backup of large systems may consume too much memory, especially if caching processes are used.

BRIEF SUMMARY

In an embodiment, a method for preventive hash loading may include receiving an indication at a storage server that a machine will be backed up. The method may further include loading fingerprints of blocks related to a previous backup of the machine to RAM of the storage server. The method may also include searching the storage server for fingerprints in the RAM that match fingerprints of incoming blocks from the machine being backed up. The method may additionally include, in response to determining that the fingerprints of the incoming blocks do not match fingerprints in the RAM, searching for the fingerprints in a database. Moreover, the method may include transferring only blocks from the machine being backed up that are not in the RAM or the database of the storage server to the storage server.

One or more of the following features may be included. The method may further include receiving backups of one or more machines at the storage server. The method may further include adding fingerprints of received blocks from the backups to the database. The method may also include calculating a hash value for contents of backed up blocks stored on the storage server. Moreover, the method may include transferring only unique data blocks that are not on the storage server or within existing backups from the machine being backed up to the storage server.

In an embodiment, a computer program product may reside on a computer readable storage medium and may have a plurality of instructions stored on it. When executed by a processor, the instructions may cause the processor to perform operations for preventive hash loading. The operations may include receiving an indication at a storage server that a machine will be backed up. The operations may further include include loading fingerprints of blocks related to a previous backup of the machine to RAM of the storage server. The operations may also include searching the storage server for fingerprints in the RAM that match fingerprints of incoming blocks from the machine being backed up. The operations may additionally include, in response to determining that the fingerprints of the incoming blocks do not match fingerprints in the RAM, searching for the fingerprints in a database. Moreover, the operations may include transferring only blocks from the machine being backed up that are not in the RAM or the database of the storage server to the storage server.

One or more of the following features may be included. The operations may include receiving backups of one or more machines at the storage server. The operations may further include adding fingerprints of received blocks from the backups to the database. The operations may also include calculating a hash value for contents of backed up blocks stored on the storage server. Moreover, the operations may include transferring only unique data blocks that are not on the storage server or within existing backups from the machine being backed up to the storage server.

In an embodiment, a computing system for preventive hash loading may include one or more processors. The one or more processors may be configured to receive an indication at a storage server that a machine will be backed up. The one or more processors may further be configured to load fingerprints of blocks related to a previous backup of the machine to RAM of the storage server.

The one or more processors may also be configured to search the storage server for fingerprints in the RAM that match fingerprints of incoming blocks from the machine being backed up. The one or more processors may additionally be configured to, in response to determining that the fingerprints of the incoming blocks do not match fingerprints in the RAM, search for the fingerprints in a database. Moreover, the one or more processors may be configured to transfer only blocks from the machine being backed up that are not in the RAM or the database of the storage server to the storage server.

One or more of the following features may be included. The one or more processors may be configured to receive backups of one or more machines at the storage server. The one or more processors may be further configured to add fingerprints of received blocks from the backups to the database. The one or more processors may also be configured to calculating a hash value for contents of backed up blocks stored on the storage server. Moreover, the one or more processors may be configured to transfer only unique data blocks that are not on the storage server or within existing backups from the machine being backed up to the storage server.

In an embodiment, a system for preventive hash loading may include a backup agent configured to perform backups. The system may further include a storage server that received the backups. The system may also include a database for storing fingerprints of blocks received during the backups. Additionally, the system may include a RAM in the storage server for loading fingerprints of blocks corresponding to a previous backup of a machine being backed up.

The details of one or more implementations are set forth in the accompanying drawings and the description below. Other features and advantages will become apparent from the description, the drawings, and the claims.

DETAILED DESCRIPTION

Overview

Figure 1:
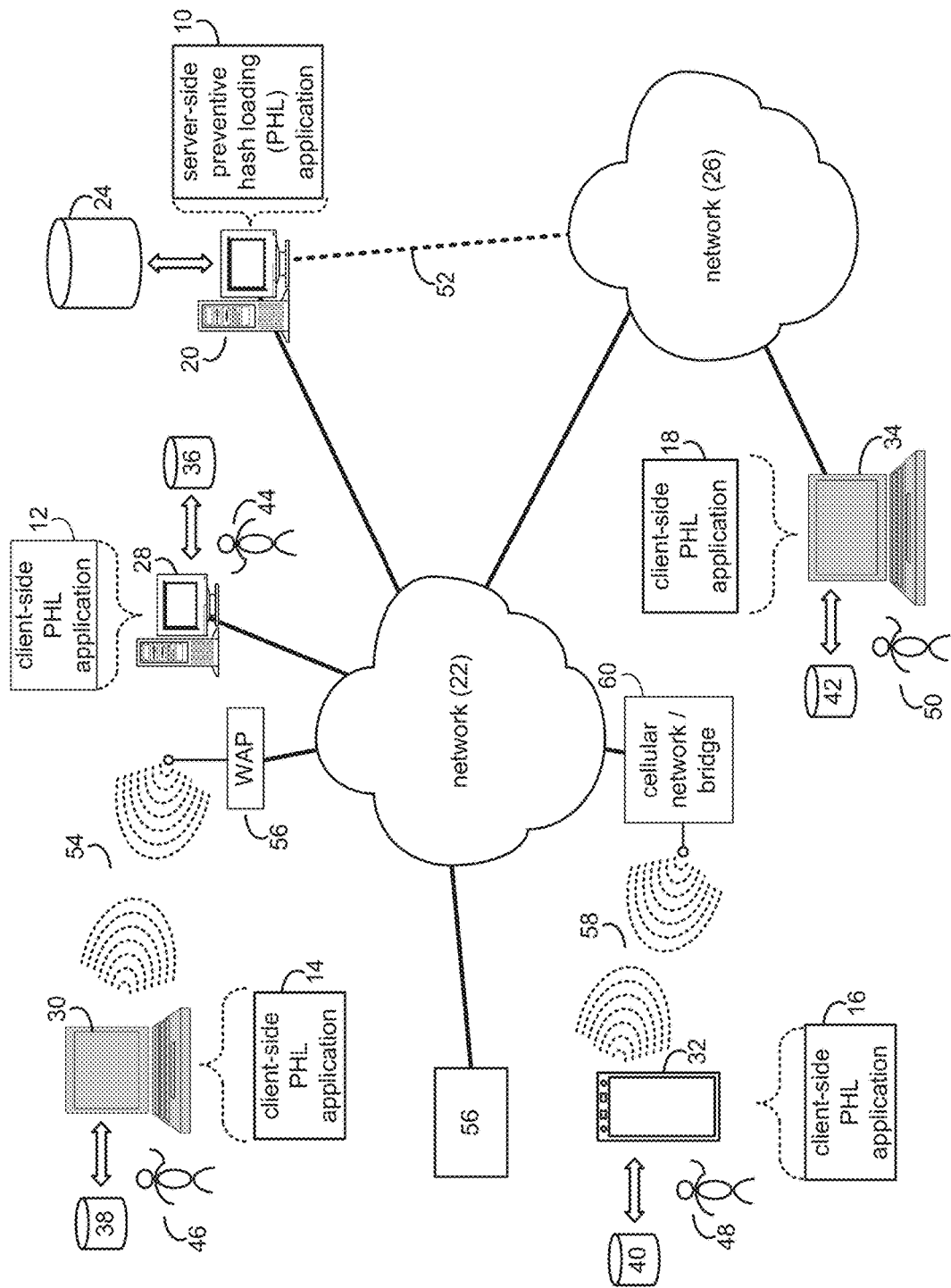
FIG. 1 depicts an example system that can execute implementations of the present disclosure.

A cloud provider or system administrator may institute backup and recovery procedures to ensure persistence of applications, data, or other resources accessed through one or more physical or virtual machines. For example, a backup archive of the physical or virtual machine may be created and stored onsite or offsite and may include the entire content of the physical or virtual machine before it failed. Efficient recovery of physical or virtual machines may be critical for proper business or other operations of an organization as application demands are likely to continue in the event of a physical or virtual machine failure.

Businesses and other organizations may have large amounts of data to backup and may make create backups often. Further, their data content may change quickly, which may require more backups to be created. Transmitting less data during a backup may free resources such as storage space, CPU time etc. During a backup, for each block of data, a hash may be calculated. Compare operations may be performed on a client side or a server side and may determine whether data requested by a server already exists there. A client may send a request to a server to compare new hashes with existing hashes, and depending on the results, may send the data to the server (or storage device) for backup. For example, if the data does not exist on the server (or storage device) based on the compare operation, the client may send the data. If the data does exist on the server, the client may not send the data based on the compare operation.

During a backup, deduplication techniques may be used to reduce the amount of data transferred or transmitted. For example, a hash calculation of backed up data blocks on the client side may be performed and it may be verified that the server, which may include storage that keeps the backed up data, does not have the same data. Blocks may be backed up by first comparing a client-computed hash and a hash from the server. Hashes existing on the server may be checked against hashes of data for backup on a client. Hashes sent during backup may be added to a cache and the blocks need not be sent again in a later backup if they have already been added to the cache (i.e., the blocks have been saved already).

One drawback of deduplication may relate to speed of the deduplication process and extra traffic that may travel through the network, which may lead to network overload. This may be most sensitive to large backed up sizes and backups of large quantities of machines. Further, extra data traffic on the network may lead to slow backups due to network overload. If a user has a backup time window, then a slow backup take more time than allowed for by the backup time window.

Without using a hash-table as described herein, a storage server may refers to fingerprint database directly to fulfill a data request. The database may be large (e.g., a dozen gigabytes and more) and access to huge data base may be very slow. Creation of a fast hash-table on client (e.g., uploading a hash-table to client) and comparing fingerprints on client side may not be applicable for large backups as it may require too much RAM on the client. Further, even there is enough RAM for the backup, it may not be acceptable to store such a high data capacity in RAM permanently. Further, a permanently sending the hash data over the network may be required. A user may purchase additional equipment to increase computing speed but new resources may require additional costs.

By creating a fingerprint cache (e.g., rating hash table, for example) in the RAM of a storage server and dynamically replenishing the fingerprint cache depending on the backed up data blocks (this may be referred to as cache warming), the aforementioned network traffic may be reduced. A hash-table may have quick reaction time in response to a request. Further, the hash-table may make usage more effective than requests to a fingerprint database directly. The hash-table may include hashes of recently backed up blocks and the most frequency used hashes.

In a situation with a huge data capacity, information about rarely used caches, or caches that have not been used for a long time, may be removed from hash-table. When a machine that has not been backed up for a long time is being backed up backup, a storage server may dynamically (e.g., by request from a backup agent on a remote machine) fill a hash-table in its RAM by caching a previous backup of the same machine (i.e., warming up the cache). These caches may most likely be present in the new backup. In this way, the techniques and features described herein should increase the chances of a positive response to request from the cache and may avoid using a fingerprint database to capture the requested data. Using the techniques and features described here via an application on the storage server, faster reactions to a client's (being backed up) requests may be realized and increase in backup and deduplication speed overall may be achieved.

Referring to FIG. 1, there is shown a server-side preventive hash loading (PHL) application 10 and client-side PHL applications 12, 14, 16, and 18. Server application 10 and/or one or more of client applications 12, 14, 16, and/or 18 may execute one or more processes configured to carry out one or more of the features described herein. Server application 10 may be referred to as a process configured to carry out one or more of the features described herein, such as PHL process 10. Further, one or more of client applications 12, 14, 16, and 18 may be referred to as a process configured to carry out one or more of the features described herein, such as PHL processes 12, 14, 16, and/or 18.

As will be discussed below and referring now to FIG. 2, PHL process or application 10, 12, 14, 16, or 18 may receive 200 backups of one or more machines at the storage server. PHL process 10, 12, 14, 16, or 18 may also add 202, fingerprints of received blocks from the backups to the database. PHL process 10, 12, 14, 16, or 18 may further, receive 204 an indication at a storage server that a machine will be backed up. Additionally, PHL process 10, 12, 14, 16, or 18 may load 206 fingerprints of blocks related to a previous backup of the machine to RAM of the storage server. Moreover, PHL process 10, 12, 14, 16, or 18 may search 208 the storage server for fingerprints in the RAM that match fingerprints of incoming blocks from the machine being backed up. Further, PHL process 10, 12, 14, 16, or 18 may, in response to determining that the fingerprints of the incoming blocks do not match fingerprints in the RAM, search 210 for the fingerprints in a database. PHL process 10, 12, 14, 16, or 18 may also transfer 212 only blocks from the machine being backed up that are not in the RAM or the database of the storage server to the storage server. Additionally, PHL process 10, 12, 14, 16, or 18 may calculate 214 a hash value for contents of backed up blocks stored on the storage server. Moreover, PHL process 10, 12, 14, 16, or 18 may transfer 216 only unique data blocks that are not on the storage server or within existing backups from the machine being backed up to the storage server.

The PHL process may be a server-side process (e.g., server-side PHL process 10), a client-side process (e.g., client-side PHL process 12, client-side PHL process 14, client-side PHL process 16, or client-side PHL process 18), or a hybrid server-side/client-side process (e.g., a combination of server-side PHL process 10 and one or more of client-side PHL processes 12, 14, 16, 18).

System Overview

Referring to FIG. 1, server-side PHL process 10 may reside on and may be executed by server computer 20, which may be in communication with network 22 (e.g., the Internet or a local area network). Examples of server computer 20 may include, but are not limited to: a personal computer, a server computer, a series of server computers, a mini computer, and/or a mainframe computer. The server computer 20 may be a distributed system and the operations of server computer 20 may execute on one or more processors, simultaneously and/or serially. For example, server computer 20 may be a symbolic representation of a cloud computing site, cloud environment, or cloud platform running multiple servers, computers, or virtual machines (e.g., a virtual machine host computer). Server computer 20 may execute one or more operating systems, examples of which may include but are not limited to: Microsoft Windows Server™; Novell Netware™; Redhat Linux™, Unix, or a custom operating system, for example.

The instruction sets and subroutines of server-side PHL process 10, which may be stored on storage device 24 coupled to server computer 20, may be executed by one or more processors (not shown) and one or more memory architectures (not shown) incorporated into server computer 20. Storage device 24 may include but is not limited to: a hard disk drive; a tape drive; an optical drive; a solid state storage device; a RAID array; a random access memory (RAM); and a read-only memory (ROM).

Server computer 20 may execute a web server application that allows for access to server computer 20 (via network 22) using one or more protocols, examples of which may include but are not limited to HTTP (i.e., HyperText Transfer Protocol). Network 22 may be in communication with one or more secondary networks (e.g., network 26), examples of which may include but are not limited to: a local area network; a wide area network; or an intranet, for example.

Client-side PHL processes 12, 14, 16, 18 may reside on and may be executed by client electronic devices 28, 30, 32, and/or 34 (respectively), examples of which may include but are not limited to personal computer 28, a television with one or more processors embedded therein or coupled thereto (not shown), laptop computer 30, data-enabled mobile telephone 32, notebook computer 34, a tablet (not shown), and a personal digital assistant (not shown), for example. Client electronic devices 28, 30, 32, and/or 34 may each be in communication with network 22 and/or network 26 and may each execute an operating system, examples of which may include but are not limited to Apple iOS™, Microsoft Windows™, Android™, Redhat Linux™, or a custom operating system.

The instruction sets and subroutines of client-side PHL processes 12, 14, 16, 18, which may be stored on storage devices 36, 38, 40, 42 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Storage devices 36, 38, 40, 42 may include but are not limited to: hard disk drives; tape drives; optical drives; solid state storage devices; RAID arrays; random access memories (RAM); read-only memories (ROM); compact flash (CF) storage devices; secure digital (SD) storage devices; and memory stick storage devices.

Client-side PHL processes 12, 14, 16, 18 and/or server-side PHL process 10 may be processes that run within (i.e., are part of) a cloud computing site, cloud computing application, cloud platform, or cloud environment. Alternatively, client-side PHL processes 12, 14, 16, 18 and/or server-side PHL process 10 may be stand-alone applications that work in conjunction with the cloud computing site, cloud computing application, cloud platform, or cloud environment. One or more of client-side PHL processes 12, 14, 16, 18 and server-side PHL process 10 may interface with each other (via network 22 and/or network 26).

Users 44, 46, 48, 50 may access server-side PHL process 10 directly through the device on which the client-side PHL process (e.g., client-side PHL processes 12, 14, 16, 18) is executed, namely client electronic devices 28, 30, 32, 34, for example. Users 44, 46, 48, 50 may access server-side PHL process 10 directly through network 22 and/or through secondary network 26. Further, server computer 20 (i.e., the computer that executes server-side PHL process 10) may be in communication with network 22 through secondary network 26, as illustrated with phantom link line 52.

The various client electronic devices may be directly or indirectly coupled to network 22 (or network 26). For example, personal computer 28 is shown directly coupled to network 22 via a hardwired network connection. Further, notebook computer 34 is shown directly coupled to network 26 via a hardwired network connection. Laptop computer 30 is shown wirelessly coupled to network 22 via wireless communication channel 54 established between laptop computer 30 and wireless access point (i.e., WAP) 56, which is shown directly coupled to network 22. WAP 56 may be, for example, an IEEE 802.11a, 802.11b, 802.11g, 802.11n, Wi-Fi, and/or Bluetooth device that is capable of establishing a wireless communication channel 54 between laptop computer 30 and WAP 56. Data-enabled mobile telephone 32 is shown wirelessly coupled to network 22 via wireless communication channel 58 established between data-enabled mobile telephone 32 and cellular network/bridge 60, which is shown directly coupled to network 22.

All of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. Bluetooth is a telecommunications industry specification that allows e.g., mobile phones, computers, and personal digital assistants to be interconnected using a short-range wireless connection.

PHL Process

For the following discussion, client-side PHL process 12 will be described for illustrative purposes and client computer 28 may run client-side PHL application 12 to carry out some or all of the techniques and features described here. It should be noted that client-side PHL process 12 may interact with server-side PHL process 10 and may be executed within one or more applications that allow for communication with server-side PHL process 10. However, this is not intended to be a limitation of this disclosure, as other configurations are possible (e.g., stand-alone, client-side PHL processes and/or stand-alone server-side PHL processes). For example, some implementations may include one or more of client-side PHL processes 14, 16, and 18 and server-side PHL process 10 in place of or in addition to client-side PHL process 12.

The systems and methods (e.g., PHL process 12) described herein relate to the backup of physical or virtual machines and/or physical or virtual machine disks, drives, files, and/or folders. The systems described herein may include one or more memory elements for backup of software, databases, and physical or virtual machines, and computer storage products including instructions to be executed by a processor to cause the processor to implement the methods described herein.

Referring now to FIG. 1, one or more of users 44, 46, 48, and 50 may be cloud administrators or system administrators or may be cloud or system end-users. Referring now also to FIG. 4, the cloud or system administrators may access and administer server computer 20 or client electronic devices 28, 30, 32, 34 (respectively). In an embodiment one or more of server computer 20 or client electronic devices 28, 30, 32, 34 may be a physical computer system, virtualization host device, or cloud computing client. The virtualization host device may include a virtual machine and may run a cloud or virtualization application such as VMWare™ or may include a bare-metal embedded hypervisor (e.g. VMware™ ESX™ and VMware™ ESXi™). Further, the virtualization host device may include a vCloud™ architecture that may enhance cooperation between hypervisors. PHL processes 10, 12, 14, 16, and/or 18 may include or may work in connection with an agent (e.g., a software module), which may include or may be configured to perform any number of the techniques or features described herein.

PHL processes 10, 12, 14, 16, and/or 18 may include a software component, executable code, function, subroutine, or other set of instructions designed to carry out one or more operations for rating hash tables and reducing an amount of data transmitted during a backup process. For example, PHL process 12 may coordinate a backup and/or restore process.

A physical or virtual machine may run, for example, business critical applications for which physical or virtual machine files may need to be backed up, recovered and/or restored upon a failure. The physical or virtual machine files may be backed up before a system failure. A backup operation or process may be initiated by a user. The user may select an entire disk or drive to be backed up, or may select a portion of the disk or drive to be backed up. In an implementation, the user may select one or more files or folders for backup. In response to receiving instructions for backup, a physical or virtual machine may begin a backup process.

A cache may be created on a client computer or cloud computing client that needs to be backed up. A rating hash table may be an implementation of such a cache. To reduce memory consumption, a cache which keeps information about the latest hashes or most often requested hashes (or e.g., least recently used (LRU) or least frequently used (LFU)) may be used. For example, a rating hash table, may be used.

PHL process 12 as described herein may be a process that may help to reduce the amount of data transmitted during a backup process over a network. For example, a client computer or cloud computing client may have a portion of software that prepares data for backup, and PHL process 12 may be a portion of that software.

For example, if data on the client side is frequently used or requested, then it may not be necessary to compare this data with data on the server because it is likely that this data is already stored at the server. Thus, some data can be eliminated from the set of data transmitted for the compare operation of the backup process. Using a rating process to assign higher ratings for the more frequently used or requested data may help determine which data does not needed to be transmitted between the client and the server for the compare operation of the backup process. Hashes with higher ratings have likely already been sent to the server, and the server will have already cached those hashes. The hashes with the higher ratings may correspond to data that is likely already in the server because several clients (e.g., cloud computing clients) may have the same or similar data or run similar applications. These clients may have already been backed up to the server during a previous backup of an incremental backup process, and thus most of the data may already be at the server. Because the backup may be incremental, most of the data besides data that changed may already be at the server.

Figure 2:
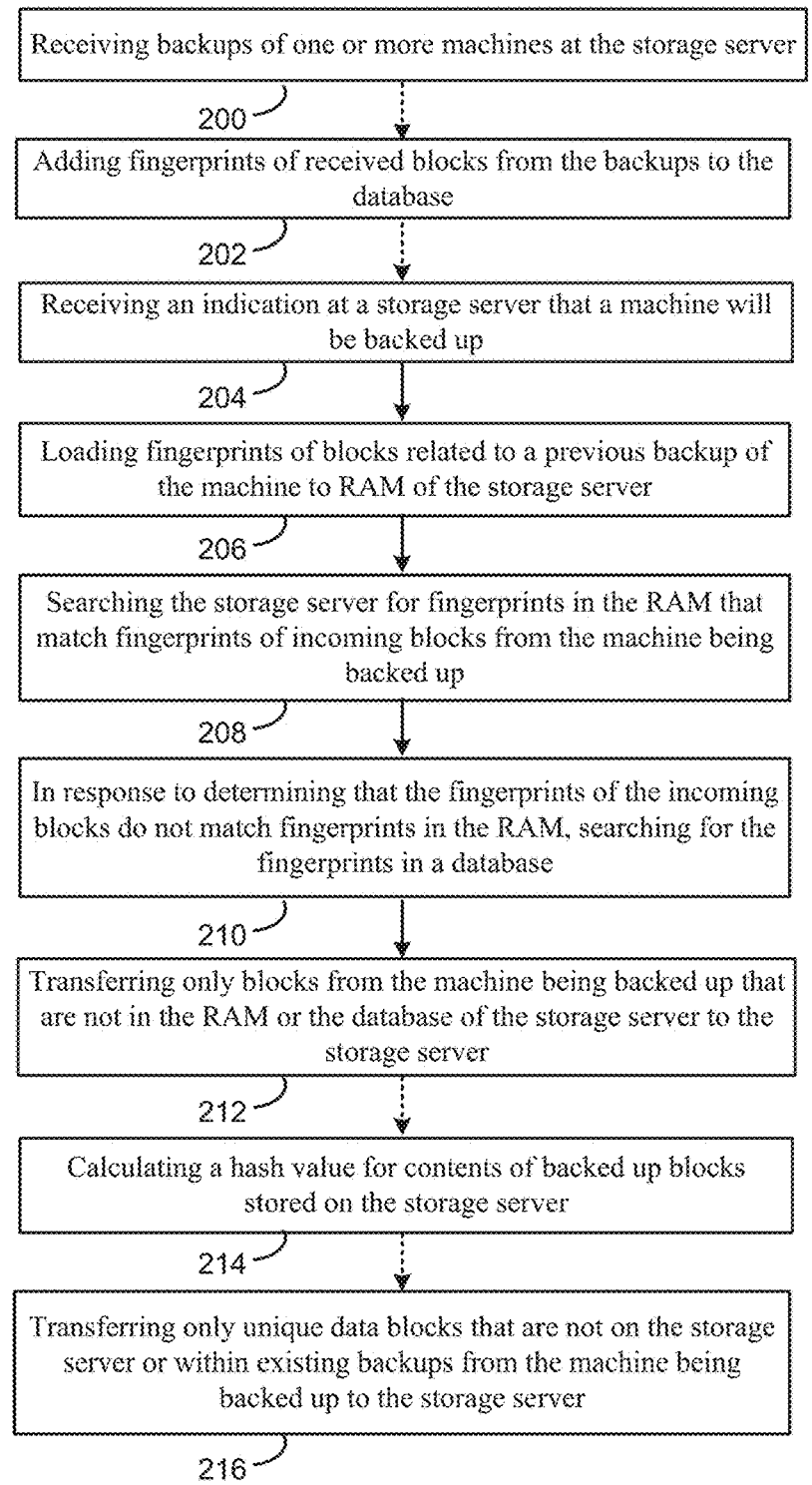
FIG. 2 is a diagrammatic flowchart illustrating a process in accordance with implementations of the present disclosure.
Figure 3:
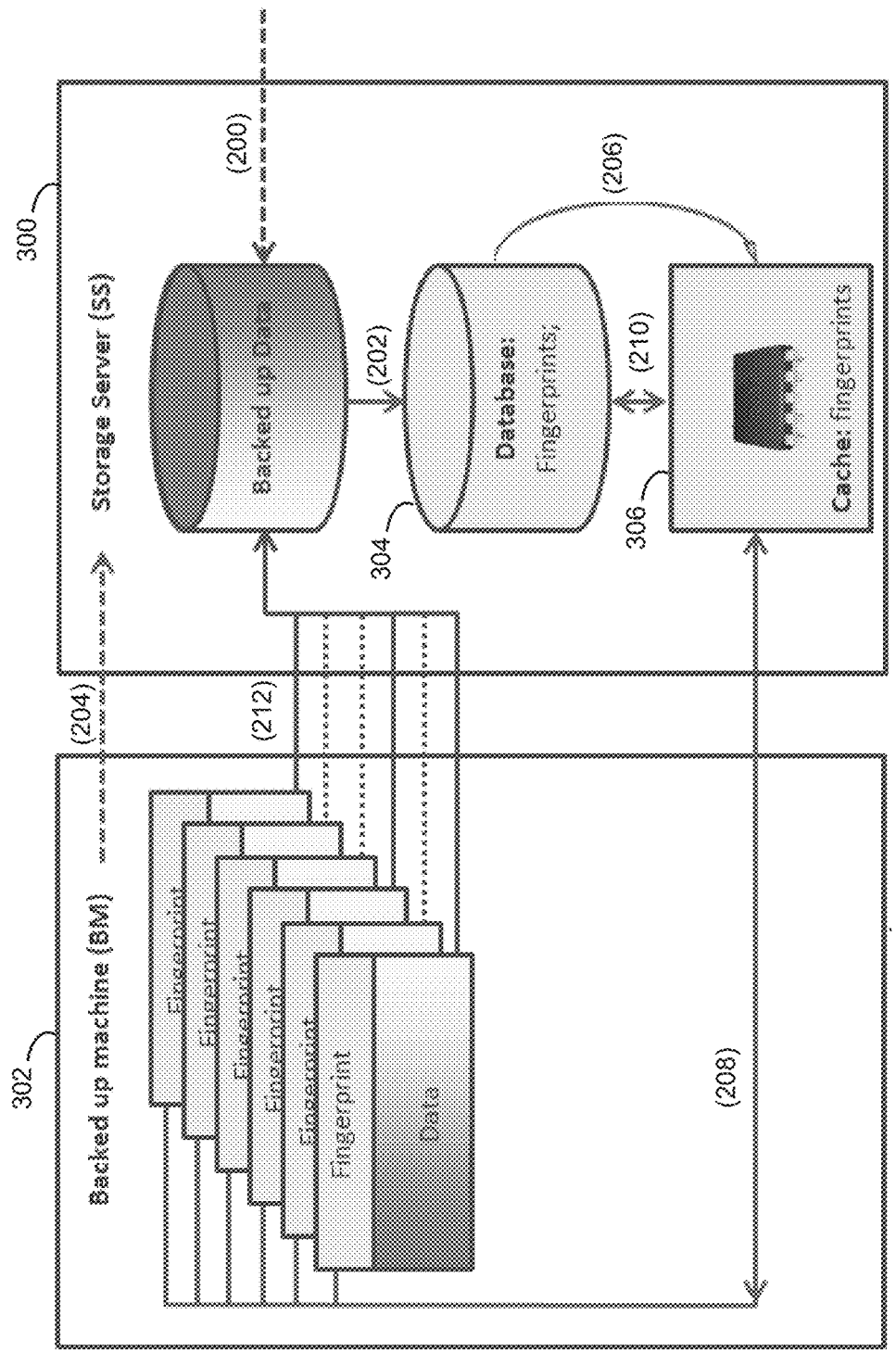
FIG. 3 also depicts an example system that can execute implementations of the present disclosure.

Referring now to FIGS. 2 and 3, PHL process 12 may work with or be a component of a backup agent configured to execute the techniques and features described herein. PHL process 12 may receive 200 backups of one or more machines at the storage server 300. The backups may be stored permanently. PHL process 12 may also add 202 fingerprints of received blocks from the backups to the database 304. The database 304 may be an inner database. In embodiments, the database 304 may be either local or external storage.

For example, PHL process 12 may calculate 214 a hash value for contents of backed up blocks stored on the storage server 300 (i.e., from all or most of the previous backups). This may be referred to as a fingerprint. The fingerprints with block offsets may be stored in the inner database.

Further, PHL process 12 may receive 204 an indication at the storage server 300 that a machine 302 will be backed up. The indication may be received via the backup agent. Additionally, PHL process 12 may load 206 fingerprints of blocks related to a previous backup of the machine 302 to RAM 306 of the storage serve 300. In an embodiment, the fingerprints may be a rating hash table that also may include recently used fingerprints and most often used fingerprints. For example, PHL process 12 may calculate fingerprints (e.g., a hash-table, hash-filter, hash-set description, etc.) of backed up data (e.g., a disk or a file) whose stream may travel through the network.

PHL process 12 may also search 208 (or, e.g., query) the storage server 300 for fingerprints in the RAM 306 that match fingerprints of incoming blocks from the machine 300 being backed up. This may be done prior to, or during, the backup. Further, PHL process 12 may, in response to determining that the fingerprints of the incoming blocks do not match fingerprints in the RAM 306, search 210 for the fingerprints in a database 304. In other words, PHL process 12 may compare the incoming fingerprints to the fingerprints in the RAM 306 and database 304 that are from previous backups to determine if the incoming fingerprints are present. If the incoming fingerprints are present in the RAM 306 or database 304, it is not necessary to transfer (e.g., via the network) the blocks corresponding to those fingerprints already present from the machine 302 being backed up to the storage server 300. Further, since access to RAM 306 is faster than access to database 304 (especially a huge database) the deduplication process may be accelerated.

The incoming blocks from the machine 302 being backed up may not be found in the RAM 306 or the database 304. In this case, PHL process 12 may transfer 212 only blocks from the machine 302 being backed up that are not in the RAM 306 or the database 304 of the storage server 300 to the storage server 300. For example, PHL process 12 may transfer 216 only unique data blocks that are not on the storage server 300 or within existing backups from the machine 302 being backed up to the storage server 300.

In an embodiment, fingerprints may be generated and stored on a storage server as a hash table in different forms. For example, a pure hash list or a rated hash list may be used. Depending on the hash container form coming from the server, the server may use it as is, or may convert the incoming hash to a rating hash table.

Further, the techniques and features described herein may be applied to local and network attached storage, which may require an intensive deduplication of data stored thereon. The result may be higher backup speed and less storage space consumed.

Additionally, the techniques and features described herein may be applied to cloud storage, which may include a huge volume of data. Cloud storage may generally be relatively slower than local and network attached storage. Thus, decreasing the amount of data sent may result in more efficient and faster data archiving.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention. In certain embodiments, a "module" may include software, firmware, hardware, or any reasonable combination thereof.

Various embodiments of the systems and methods may include and/or utilize a computer device. In various embodiments, a computer may be in communication with a server or server system utilizing any suitable type of communication including, for example, wired or wireless digital communications. In some embodiments, the server or server system may be implemented as a cloud computing application or in a similar manner and may provide various functionality of the systems and methods as SaaS.

The examples presented herein are intended to illustrate potential and specific implementations of the present invention. The examples are intended primarily for purposes of illustration of the invention for those skilled in the art. No particular aspect or aspects of the examples are necessarily intended to limit the scope of the present invention.

The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present invention, and therefore, a more detailed description of such elements is not provided herein.

The processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary.

A "computer," "computer system," "component," "computer device," or "processor" may be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media. In various embodiments, a "host," "engine," "loader," "filter," "platform," or "component" may include various computers or computer systems, or may include a reasonable combination of software, firmware, and/or hardware.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it may be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET, SQL, MySQL, or HTML using, for example, conventional or object-oriented techniques. Programming languages for computer software and other computer-implemented instructions may be translated into machine language by a compiler or an assembler before execution and/or may be translated directly at run time by an interpreter.

Examples of assembly languages include ARM, MIPS, and x86; examples of high level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. As the systems and methods described herein aim to minimize I/O transactions, they may be useful in situations, such as cloud computing configurations, where I/O transactions are performed over a WAN or other network with long I/O delays. The network may use routers and/or public communication links. One type of data communication network may cover a relatively broad geographic area (e.g., city-to-city or country-to-country) which uses transmission facilities provided by common carriers, such as telephone service providers.

In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods, systems, and tools described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier or other data location information as described herein). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

As employed herein, an application server may be a server that hosts an API to expose business logic and business processes for use by other applications. Examples of application servers include J2EE or Java EE 5 application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java).

Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Implementations of the present disclosure and all of the functional operations provided herein can be realized in digital electronic circuitry, or in computer software, firmware, or hardware, including the structures disclosed in this specification and their structural equivalents, or in combinations of one or more of them. Implementations of the disclosure can be realized as one or more computer program products, i.e., one or more modules of computer program instructions encoded on a computer readable medium for execution by, or to control the operation of, a data processing apparatus. The computer readable medium can be a machine-readable storage device, a machine readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions or computer program products and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. These may also be referred to as computer readable storage media. The processor and the memory can be supplemented by, or incorporated in, special purpose logic circuitry.

To provide for interaction with a user, implementations of described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations of the present disclosure can be realized in a computing system that includes a back end component, e.g., as a data server, or that includes a middleware component, e.g., an application server, or that includes a front end component, e.g., a client computer having a graphical user interface or a Web browser through which a user can interact with an implementation of the present disclosure, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this disclosure contains many specifics, these should not be construed as limitations on the scope of the disclosure or of what may be claimed, but rather as descriptions of features specific to particular implementations of the disclosure. Certain features that are described in this disclosure in the context of separate implementations can also be provided in combination in a single implementation. Conversely, various features that are described in the context of a single implementation can also be provided in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

While various embodiments have been described herein, it should be apparent, however, that various modifications, alterations and adaptations to those embodiments may occur to persons skilled in the art with the attainment of some or all of the advantages of the invention. The disclosed embodiments are therefore intended to include all such modifications, alterations and adaptations without departing from the scope and spirit of the invention. Accordingly, other embodiments and implementations are within the scope of the following claims. For example, the actions recited in the claims can be performed in a different order and still achieve desirable results.

What is claimed is:

1. A method for preventive hash loading, the method comprising:
   receiving an indication at a storage server that a machine will be backed up, wherein the storage server is connected to the one or more machines by one or more networks;
   creating a fingerprint cache in RAM using a backup agent;
   loading fingerprints of blocks related to a previous backup of the machine to the fingerprint cache of the storage server;
   searching the storage server for fingerprints in the fingerprint cache that match fingerprints of incoming blocks from the machine being backed up;
   in response to determining that the fingerprints of the incoming blocks do not match fingerprints in the fingerprint cache, searching for the fingerprints in a database; and
   increasing speed of backing up the machine by transferring only blocks from the machine being backed up that are not in the fingerprint cache or the database of the storage server to the storage server, wherein searching fingerprint cache is faster than searching database.

2. The method of claim 1, further comprising:
   receiving backups of one or more machines at the storage server, wherein fingerprints are processed using a hash-filter.

3. The method of claim 2, further comprising:
   adding fingerprints of received blocks from the backups to the database.

4. The method of claim 1, further comprising:
   calculating a hash value for contents of backed up blocks stored on the storage server.

5. The method of claim 1, further comprising:
   transferring only unique data blocks that are not on the storage server or within existing backups from the machine being backed up to the storage server.

6. A computer program product residing on a computer readable storage medium having a plurality of instructions stored thereon, which, when executed by a processor, cause the processor to perform operations for preventive hash loading, the operations comprising:
   receiving an indication at a storage server that a machine will be backed up;
   creating a fingerprint cache in RAM of the storage server;
   loading fingerprints of blocks related to a previous backup of the machine to the fingerprint cache;
   searching the storage server for fingerprints in the fingerprint cache that match fingerprints of incoming blocks from the machine being backed up;
   in response to determining that the fingerprints of the incoming blocks do not match fingerprints in the fingerprint cache, searching for the fingerprints in a database;
   increasing speed of backing up the machine by transferring only blocks from the machine being backed up that are not in the fingerprint cache or the database of the storage server to the storage server, wherein searching fingerprint cache is faster than searching database; and
   replenishing fingerprint cache depending on the backed up data blocks.

7. The computer program product of claim 6, wherein the operations further comprise:

receiving backups of one or more machines at the storage server, wherein fingerprints are processed using a hash-set description.

8. The computer program product of claim 7, wherein the operations further comprise:
adding fingerprints of received blocks from the backups to the database.

9. The computer program product of claim 6, wherein the operations further comprise:
calculating a hash value for contents of backed up blocks stored on the storage server.

10. The computer program product of claim 6, wherein the operations further comprise: transferring only unique data blocks that are not on the storage server or within existing backups from the machine being backed up to the storage server.

11. A computing system for preventive hash loading, the computing system comprising one or more processors, wherein the one or more processors are configured to:
receive an indication at a storage server that a machine will be backed up;
create a fingerprint cache in RAM using a backup agent;
load fingerprints of blocks related to a previous backup of the machine to the fingerprint cache of the storage server;
search the storage server for fingerprints in the fingerprint cache that match fingerprints of incoming blocks from the machine being backed up;
in response to determining that the fingerprints of the incoming blocks do not match fingerprints in the fingerprint cache, search for the fingerprints in a database; and
increase speed of backing up the machine by transferring only blocks from the machine being backed up that are not in the fingerprint cache RAM or the database of the storage server to the storage server, wherein searching fingerprint cache is faster than searching database.

12. The computing system of claim 11, wherein the one or more processors are further configured to:
receive backups of one or more machines at the storage server, wherein fingerprints are processed using a hash-table.

13. The computing system of claim 12, wherein the one or more processors are further configured to:
add fingerprints of received blocks from the backups to the database.

14. The computing system of claim 11, wherein the one or more processors are further configured to:
calculate a hash value for contents of backed up blocks stored on the storage server.

15. The computing system of claim 11, wherein the one or more processors are further configured to:
transfer only unique data blocks that are not on the storage server or within existing backups from the machine being backed up to the storage server.

16. A system for preventive hash loading, the system comprising:
a backup agent configured to perform backups of one or more machines;
a storage server that received the backups, wherein the storage server is connected to the one or more machines by one or more networks;
a database for storing fingerprints of blocks received during the backups; and
a RAM in the storage server; and
a fingerprint cache created in the RAM, the finger print cache configured to load fingerprints of blocks corresponding to a previous backup of a machine being backed up, wherein fingerprint cache is replenished depending on the backed up data blocks, wherein fingerprint cache stores hashes of recently backed up blocks and hashes of blocks that are frequently used, wherein backup agent increases speed of backing up the machine by transferring only blocks from the machine being backed up that are not in the RAM or the database of the storage server to the storage server such that hash traffic through network is reduced.

* * * * *